United States Patent [19]

Schneider et al.

[11] Patent Number: 5,801,035
[45] Date of Patent: Sep. 1, 1998

[54] L-AMINO ACID OXIDASE

[75] Inventors: Palle Schneider, Ballerup; Anders Hjelholt Pedersen, Lyngby; Svend Aage Hansen, Stenløse, all of Denmark

[73] Assignee: Novo Nordisk A/S, Bagsvaerd, Denmark

[21] Appl. No.: 535,239

[22] PCT Filed: Apr. 27, 1994

[86] PCT No.: PCT/DK94/00168
§ 371 Date: Nov. 2, 1995
§ 102(e) Date: Nov. 2, 1995

[87] PCT Pub. No.: WO94/25574
PCT Pub. Date: Nov. 10, 1994

[30] Foreign Application Priority Data

Apr. 27, 1993 [DK] Denmark ................................. 488/93

[51] Int. Cl.$^6$ .................. C12N 9/02; C12N 9/06
[52] U.S. Cl. ................................. 435/189; 435/191
[58] Field of Search ................................. 435/189, 191

[56] References Cited

U.S. PATENT DOCUMENTS 4,234,691 11/1980 Kusakabe et al. ......................... 435/191

FOREIGN PATENT DOCUMENTS 2 075 026  11/1981  United Kingdom.
WO 91/05839  5/1991  WIPO.

*Primary Examiner*—Leon B. Lankford, Jr.
*Attorney, Agent, or Firm*—Steve T. Zelson; Elias J. Lambiris

[57] ABSTRACT

An L-amino oxidase isolated from *Trichoderma harzianumi* is disclosed. The enzyme exhibits activity on L-arginine, L-lysine, L-methionine, L-asparagine, L phenylalanine, and L-leucine. The pH optimum of the enzyme is alkaline.

10 Claims, 6 Drawing Sheets

L-AMINO ACID OXIDASE

CROSS-REFERENCE TO RELATED APPLICATIONS

This application is a 371 of PCT/DK94/00168 filed Apr. 27, 1994, which is incorporated herein by reference.

TECHNICAL FIELD

The present invention relates to a novel L-Amino acid oxidase having a broad substrate specificity and being obtainable from the species *Trichoderma harzianum*. The enzyme of the invention may be used for in situ generation of hydrogen peroxide in various contexts and may be advantageously incorporated, together with a substrate, into detergent compositions which comprise also a peroxidase system for inhibiting the transfer of dye from dyed fabric to other fabrics during washing.

BACKGROUND ART

The use of bleaching agents in washing procedures and as constituents of detergent compositions is well known in the art. Thus, bleaching agents are incorporated in a large part of the commercially available detergent compositions or are sold as separate preparations designed for adding to a detergent when the wash is executed.

Bleaching agents incorporated into detergent compositions are most often precursors of hydrogen peroxide. Perborates and percarbonates are the most important examples of compounds which are employed as bleaching agents.

The original purposes of adding bleaching agents to detergents were to achieve and maintain general whiteness of garments and, more specifically, to bleach stains thereon, such as tea, coffee, fruit juices, red wine, etc.

Later, bleaching systems involving or derived from hydrogen peroxide have also been invoked for reducing dye transfer, i.e. for preventing the discoloration resulting from excess dye leaching from dyed fabrics and being deposited on other fabrics, but recently a system involving a hydrogen peroxide source and peroxidases (and possibly further components has been disclosed, vide e.g. International Patent Application WO 91/05839. One possibility for a hydrogen peroxide source taught by this patent application is an oxidase system, i.e. an oxidase together with a substrate for it. Such an oxidase must of course be compatible with the detergent matrix and, in particular, with the peroxidase system.

An L-amino acid oxidase from *Trichoderma viride*, having very high substrate-specificity to L-lysine has been reported in GB 2015532.

SUMMARY OF THE INVENTION

It has now been found that a novel L-amino acid oxidase with a very broad substrate-specificity is obtainable from *Trichoderma harzianum*. This novel enzyme possesses excellent properties for in situ generation of hydrogen peroxide.

Accordingly, the present invention provides an L-amino acid oxidase (E.C. 1.4.3.2) having a pH optimum in the range of from pH 8.5 to 9.5 (determined after incubation for 20 minutes at 20° C. in the presence of L-arginine), a pH stability of 80% or more relative to initial activity at pH 9.5 (determined after incubation for 1 hour at 40° C. in the absence of substrate), and activity towards L-arginine, L-lysine, L-methionine, L-asparagine, L-phenylalanine, and L-leucine.

In another aspect, the invention provides a process for the preparation of an L-amino acid oxidase of the invention, which process comprises cultivation of an L-amino acid oxidase producing strain of *Trichoderma harzianum*, in a suitable nutrient medium, containing carbon and nitrogen sources and inorganic salts, followed by recovery of the desired enzyme.

In a further aspect, the invention provides a detergent additive comprising an L-amino acid oxidase of the invention, the additive being provided in the form of a granulate, preferably a non-dusting granulate, a liquid, in particular a stabilized liquid, a slurry, or a protected enzyme.

In a yet further aspect, the invention provides a detergent composition comprising an L-amino acid oxidase of the invention and a substrate for the oxidase.

MICROORGANISMS

A strain of *Trichoderma harzianum* A611 was deposited on 22 Feb. 1993 according to the Budapest Treaty on the International Recognition of the Deposits of Microorganisms for the Purpose of Patent Procedures, at Centraal Bureau voor Schimmelcultures (CBS), Oosterstraat 1, 3740 AG Baarn, Netherlands under Accession No. CBS 223.93.

BRIEF DESCRIPTION OF DRAWINGS

The present invention is further illustrated by reference to the accompanying drawings, in which.

DETAILED DISCLOSURE OF THE INVENTION

The present invention provides novel L-amino acid oxidases (E.C. 1.4.3.2) that can be described by the following characteristics.

Physico-chemical Properties An L-amino acid oxidase preparation was subjected to characterization according to Example 3 of this specification.

The L-amino acid oxidase of the invention shows activity in the interval of from pH below 7 to a pH of approximately 12. The enzyme has a pH optimum in the range of from pH 8 to 10, more specifically in the range of from pH 8.5 to 9.5, around pH 9, as determined after incubation for 20 minutes at room temperature in the presence of L-arginine.

The L-amino acid oxidase of the invention has a pH stability of more than 80% relative to initial activity in the range pH 7–9.5. At pH 10 the L-amino acid oxidase of the invention has a pH stability of more than 70% relative to initial activity, preferably more than 80% relative to initial activity, as determined after incubation for 1 hour at 40° C. in the absence of substrate.

The L-amino acid oxidase of the invention is stable in a temperature interval of from below 22° C. to above 60° C. The enzyme shows a temperature stability of more than 80% relative to initial activity in the range of from 25° C. to 60° C.

The L-amino acid oxidase of the invention shows activity towards L-arginine, L-lysine, L-methionine, L-asparagine, L-phenylalanine, and L-leucine.

Immunochemical Properties

The L-amino acid oxidase of the invention has immunochemical properties identical or partially identical (i.e. at least partially identical) to those of an L-amino acid oxidase derived from the strain *T. harzianum* A611, CBS 223.93.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), Chapters 5 and 14. The terms "antigenic identity" and "partial antigenic identity" are described in the same book, Chapters 5, 19 and 20.

Monospecific antiserum is generated according to the above mentioned reference by immunizing rabbits with the purified L-amino acid oxidase of the invention. The immunogen is mixed with Freund's adjuvant and injected subcutaneously into rabbits every second week. Antiserum is obtained after a total immunization period of 8 weeks, and immunoglobulin prepared therefrom as described by Axelsen N. H., supra.

Preparation of the Enzyme

The L-amino acid oxidase of the invention is obtainable by cultivation of an L-amino acid oxidase producing strain of *Trichoderma harzianum* in a suitable nutrient medium containing carbon and nitrogen sources and inorganic salts, followed by recovery of the desired enzyme.

In a preferred embodiment, the strain *T. harzianum* A611, CBS 223.93, or a mutant or a variant thereof, is cultivated.

The L-amino acid oxidase of the invention may also be obtained by recombinant DNA-technology.

Industrial Applications

The L-amino acid oxidase of the invention may, in combination with its substrate, be implemented in processes in which in situ generation of hydrogen peroxide is desirable.

Thus, in a preferred embodiment, the L-amino acid oxidase of the invention may advantageously be incorporated into detergent compositions, in particular detergent compositions comprising peroxidase systems, e.g. for dye transfer inhibition during laundering or for improved bleaching in laundry detergents.

In other preferred embodiments, the L-amino acid oxidase of the invention may be incorporated into toothpaste, or used for preservation of cosmetics.

In yet another embodiment, the L-amino acid oxidase of the invention may be implemented in processes for treatment of waste water, for bleaching of pulp for paper production, in treatment of waste water from pulp production, and for lignin modification, e.g. in particle board production.

POD Systems

It may be desirable to utilize the L-amino acid of the invention in peroxidase systems (POD systems) for hydrogen peroxide formation.

In the context of this invention, a POD system is a system comprising an enzyme exhibiting peroxidase activity, a source of hydrogen peroxide, and optionally a peroxidase enhancing agent. Such peroxidase systems have been used for obtaining a dye transfer inhibition and have been described in e.g. International Patent Applications WO 92/18687 and WO 92/18683.

In such a peroxidase system, the enzyme exhibiting peroxidase activity may be any peroxidase enzyme comprised by the enzyme classification EC 1.11.1.7, or any fragment derived therefrom, exhibiting peroxidase activity (e.g. porphyrin ring systems or microperoxidases, cf. e.g. International Patent Applications WO 91/05858 and WO 92/16634). Such enzymes are known from microbial, plant and animal origins.

The peroxidase may be producible by plants (e.g. horseradish peroxidase) or microorganisms such as fungi or bacteria. Preferably, the peroxidase is derived from *Coprinus*, e.g. *C. cinereus* or *C. macrorhizus*, or from *Bacillus*, e.g. *B. pumilus*, particularly a peroxidase according to International Patent Application WO 91/05858.

The peroxidase may, furthermore, be one which is producible by recombinant DNA techniques. Particularly, a recombinantly produced peroxidase is a peroxidase derived from a *Coprinus* sp., in particular *Coprinus macrorhizus* or *cinereus* according to International Patent Application WO 92/16634.

In a peroxidase system, the source of hydrogen peroxide may be hydrogen peroxide or a hydrogen peroxide precursor, e.g. percarbonate or perborate, or a hydrogen peroxide generating enzyme system, e.g. an oxidase and a substrate for the oxidase.

In a peroxidase system, the enhancer may be an oxidizable substrate e.g. metal ions or phenolic compounds such as 7-hydroxycoumarin (7HCm), vanillin (VAN), and p-hydroxybenzenesulfonate (pHBS), described in e.g. International Patent Applications WO 92/18683 and WO 92/18687, and Kato M and Shimizu S, Plant Cell Physiol. 1985 26 (7), pp. 1291–1301 (cf. Table 1 in particular), or Saunders B C, et al., Peroxidase, London, 1964, p. 141 ff.

Detergent Compositions

According to the invention, the L-amino acid oxidase may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% of water and 0–30% of organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylases, lipases, cutinases, proteases, cellulases, peroxidases, and other oxidases.

In a specific aspect, the invention provides a detergent additive. The enzymes may be included in a detergent composition by adding separate additives containing one or more enzymes, or by adding a combined additive comprising all of these enzymes.

In a more specific embodiment, the invention provides a detergent additive and a detergent composition further comprising a substrate for the L-amino acid oxidase.

A suitable substrate may be one or more of L-arginine, L-lysine, L-methionine, L-asparagine, L-phenylalanine, and L-leucine.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O,2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1–2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O,2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O, 2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O, 2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g. PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O, 2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O, 2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2-3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted with percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The L-amino acid oxidase of the invention may be incorporated in concentrations conventionally employed in detergents. It is at present contemplated that, in the detergent composition of the invention, the L-amino acid oxidase may be added in an amount corresponding to 0.001–100 mg of enzyme per litre of wash liquor.

The following examples further illustrate the present invention, and they are not intended to be in any way limiting to the scope of the invention as claimed.

EXAMPLE 1

Cultivation Example

This Example illustrates the method of the present invention for the production of L-amino acid oxidase.

The seed culture was propagated in a 500 ml baffled shake flask. This was charged with 250 ml of a medium containing 2.4% of corn steep liquor, 2.4% of glucose and 0.4% of $CaCO_3$. After sterilization the medium was inoculated with mycelium from an agar slant culture of the strain T. harzianum A611, CBS 223.93. The shake flask was thereafter incubated on a shaking table for about 70 hours at 26° C.

Inoculum from this seed culture was inoculated into a 2 litre fermentor having a sterile air source and impeller agitation means. The fermentor was charged with 1.2 litre of a medium containing 10% of corn steep liquor, 0.5% of glucose, 0.5% of $(NH_4)_2SO_4$, 0.07% of $KH_2Po_4$, 0.2% of L-arginine and 1.0% of $CaCO_3$. The fermentor with medium was autoclaved for 60 minutes at 120° C.

After inoculation the temperature of the medium was maintained at 28° C. and aerated at an aeration rate of 0.8 volume of air/volume of medium/minute during fermentation. The impeller speed was 900 rpm. In the first 24 hours the pH of the fermentation medium was maintained at 6.0 by titration with a solution of 25% of glucose and 2.5% of $H_3PO_4$. From 24 hours the pH setpoint was changed to 5.8 and maintained here during the fermentation. The fermentation was allowed to proceed for about 96 hours. At this time a yield of approx. 250 mg of enzyme protein per litre was obtained.

EXAMPLE 2

Purification Example 2.7 litre of culture broth obtained according to Example 1 was adjusted to pH 5.0 and non-soluble material removed by filtration. The L-amino acid oxidase was adsorbed to approx. 270 g of solid $Ca_3(PO_4)_2$ suspended in one litre of 50 mM acetate buffer, pH 5.0. After stirring for 2 hours at room temperature, the slurry was filtered and adsorbed protein eluted with approx. 750 ml of 0.1 M sodium phosphate at pH 8.0. The buffer of the eluate was changed to 20 mM sodium phosphate, pH 7, by ultrafiltration. Finally the eluate was concentrated to 120 ml. Membrane cut off 10,000 Da.

This sample was loaded on a Q Sepharose Fast Flow column equilibrated in 20 mM sodium phosphate, pH 7.0. The column was washed with 2 column volumes of the same buffer and eluted with a gradient from 0 to 1 M NaCl in 20 mM sodium phosphate, pH 7.0. Fractions containing L-amino acid oxidase activity were pooled. The pooled protein was pure as judged by SDS-PAGE.

The specific activity of the purified L-amino acid oxidase was 16 U/mg determined in a 50 mM phosphate buffer at pH 8.5, 20° C. with 1 mM L-arginine as substrate. One unit of enzyme will form 1 μmole of hydrogen peroxide per minute. The amount of protein is quantified assuming that a solution of the L-amino acid oxidase having an optical density of 1 determined at 280 nm contains 1 mg of protein/ml. The L-amino acid oxidase yield was approx. 50 mg of pure protein per litre of culture medium.

EXAMPLE 3

Characterization Example

Characterization of the L-amino acid oxidase obtained according to the previous examples was carried out using microtiter plates. The microtiter plates were incubated at the temperature and time intervals indicated below.

Peroxidase activity was expressed in peroxidase units (PODU), one unit being defined as the amount of enzyme which, under standard conditions (i.e. pH 7.0; temperature 30° C.; reaction time 3 minutes) catalyses the conversion of 1 μmol of hydrogen peroxide per minute. The activity is determined using an assay based on ABTS (2,2'-azinobis (3ethylbenzothiazoline-6sulfonate)) as the chromophore, the greenish-blue colour produced being determined by absorbance at 418 nm.

In the following characterization experiments, detection of $H_2O_2$ was carried out using a Coprinus cinereus peroxidase (CiP), obtained according to WO 92/16634, at a level of 4.5 PODU/ml, and 0.4 mM ABTS in phosphate buffer at pH 7.0. The hydrogen peroxide concentrations were determined relative to a freshly prepared hydrogen peroxide standard solution.

pH Optimum

The assay was carried out in two steps. In a first step, the L-amino acid oxidase was incubated for 20 minutes with 1 mM of L-arginine in 100 mM of phosphate buffer at various pH. In a second step, the generated hydrogen peroxide was detected as described above.

Figure 1:
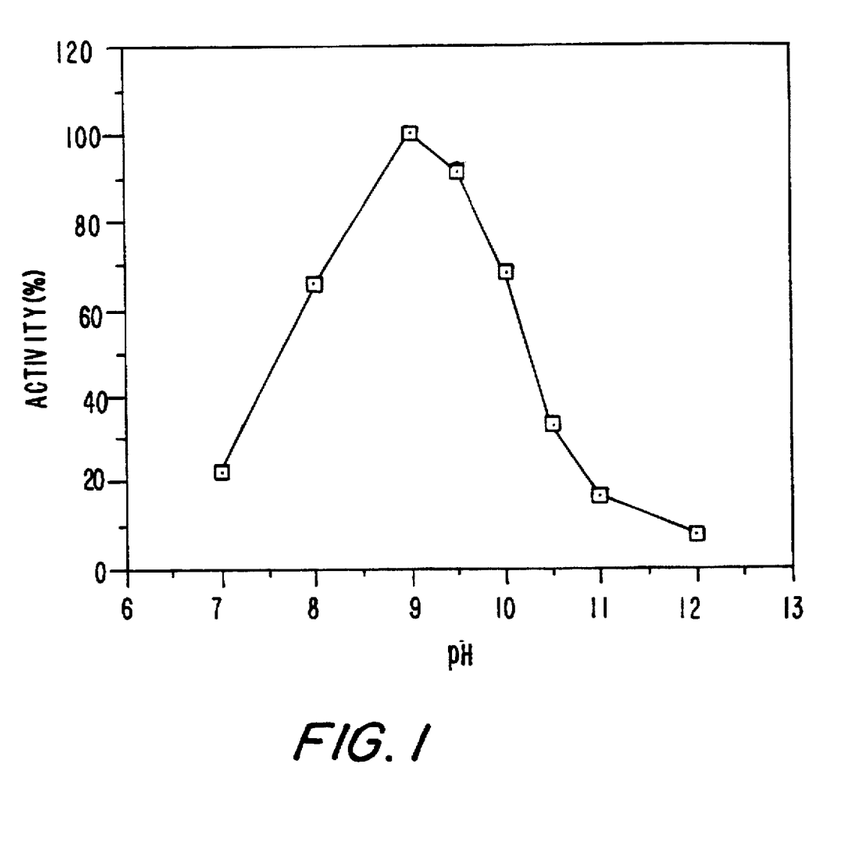
FIG. 1 shows the pH activity profile (% activity) of an L-amino acid oxidase of the invention.

The results are presented in FIG. 1. As determined by this test, the L-amino acid oxidase of the invention shows activity in the interval of from pH below 7 to a pH of approximately 12. The enzyme has a pH optimum in the range of from pH 8 to 10.

pH Stability

The L-amino acid oxidase was incubated at various pH values for 1 hour at 40° C. in 50 mM of phosphate buffer. After dilution, residual activity was measured using the two-step procedure described above.

Figure 2:
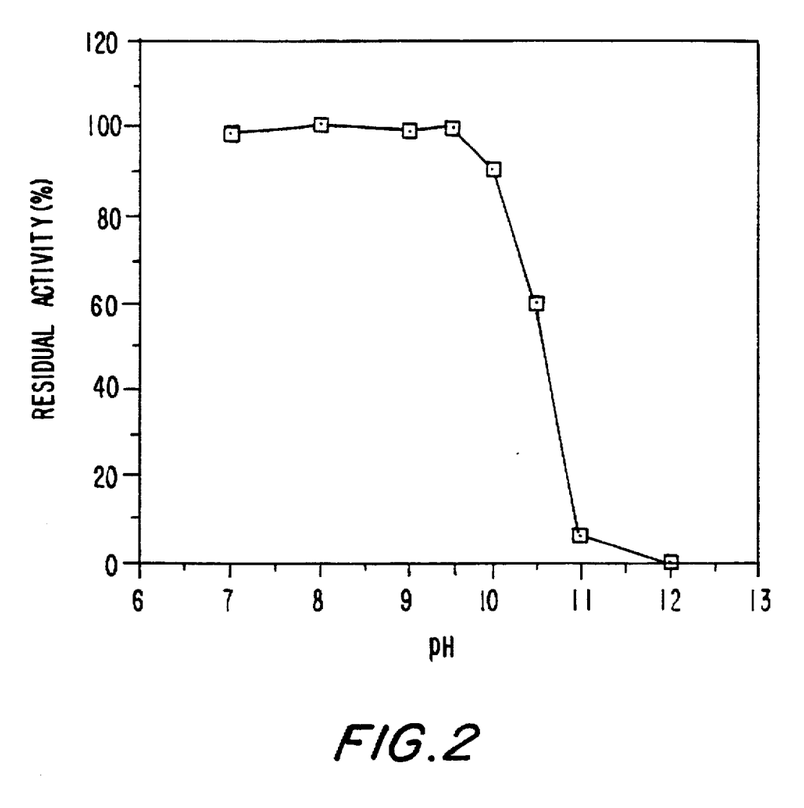
FIG. 2 shows the pH stability (% residual activity) of an L-amino acid oxidase of the invention.

The results are presented in FIG. 2. As determined by this test, the L-amino acid oxidase of the invention has a pH stability of more than 80% relative to initial activity in the range pH 7–9.5. At pH 10 the L-amino acid oxidase of the invention has a pH stability of more than 70% relative to initial activity, preferably more than 80% relative to initial activity.

Temperature Stability

The L-amino acid oxidase was incubated in phosphate buffer at pH 8.5 for 1 hour at various temperatures. After dilution, residual activity was measured using the two-step procedure described above.

Figure 3:
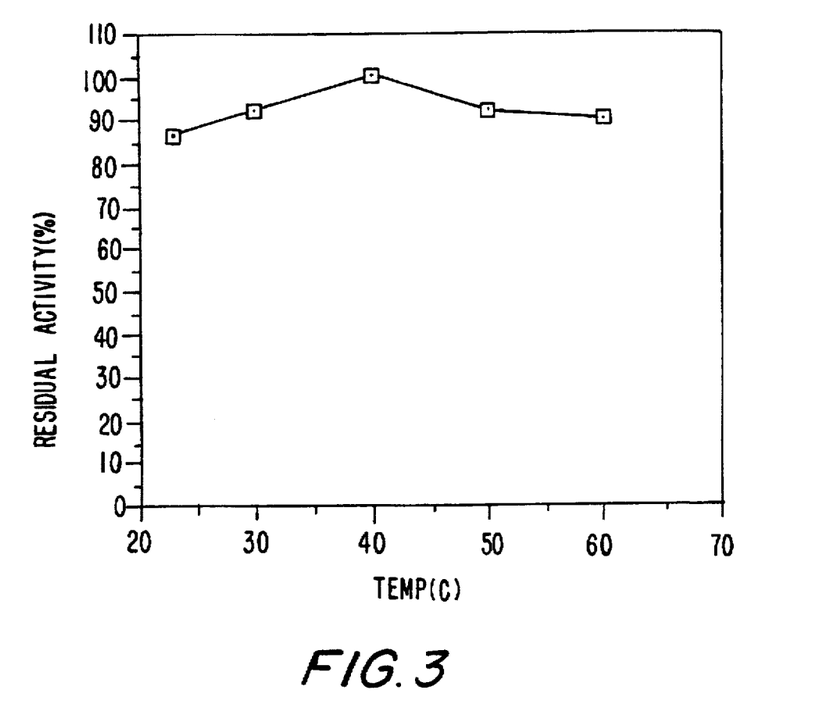
FIG. 3 shows the temperature stability (% residual activity) of an L-amino acid oxidase of the invention.

The results are presented in FIG. 3. As determined by this test, the L-amino acid oxidase of the invention is stable in a temperature interval of from below 22° C. to above 60° C.

The enzyme shows a temperature stability of more than 80% relative to initial activity in the range of from 25° C. to 60° C.

Substrate Specificity

The activity of the L-amino acid oxidase was determined with various L-amino acids as substrates. The L-amino acid oxidase was incubated with substrate in a phosphate buffer at pH 8.5 and room temperature for 20 minutes. Generated hydrogen peroxide was detected using ABTS and CiP as described above. The specific activity was determined as described in Example 2 above.

Km values for the various substrates were determined by plotting values of 1/v versus 1/s (Lineweaver-Burk plots).

The results are presented in Table 1, below.

TABLE 1

Substrate Specificity

| Substrate | Substrate Conc. (m/M) | Specific Activity (U/mg) | Km (mM) |
|---|---|---|---|
| L-leucine | 80 | 16 | 40 |
| L-phenylalanine | 80 | 25 | 25 |
| L-methionine | 80 | 8 | 15 |
| L-arginine | 10 | 30 | 1.2 |
| L-arginine | 1 | 16 | — |
| L-lysine | 1 | 7 | 0.2 |
| L-asparagine | 80 | 7 | 20 |

From Table 1 it appears that arginine and lysine show the lowest Km-values, and are, hence, expected to be preferred substrates with respect to high specific activity at low substrate concentration, as also evidenced from the specific activity stated in Table 1.

From these experiments the preferred substrate seems to be L-arginine.

EXAMPLE 4

Compatibility with Accelerated POD Systems

To investigate the compatibility of the L-amino acid oxidase of the invention with an accelerated peroxidase system (POD system), the enzyme activity at pH 8.5 was monitored for 10 minutes by simultaneous detection of hydrogen peroxide.

8 μg/ml of L-amino acid oxidase obtained according to Example 2 was added to a POD system consisting of a Coprinus Cinereus peroxidase (CiP), obtained according to WO 92/16634, in an amount of 5 PODU/ml, and 1.7 mM ABTS in phosphate buffer at pH 8.5±50 μM p-hydroxybenzenesulfonate (PHBS) as accelerator, and containing 1 mM L-leucine.

Figure 4A:
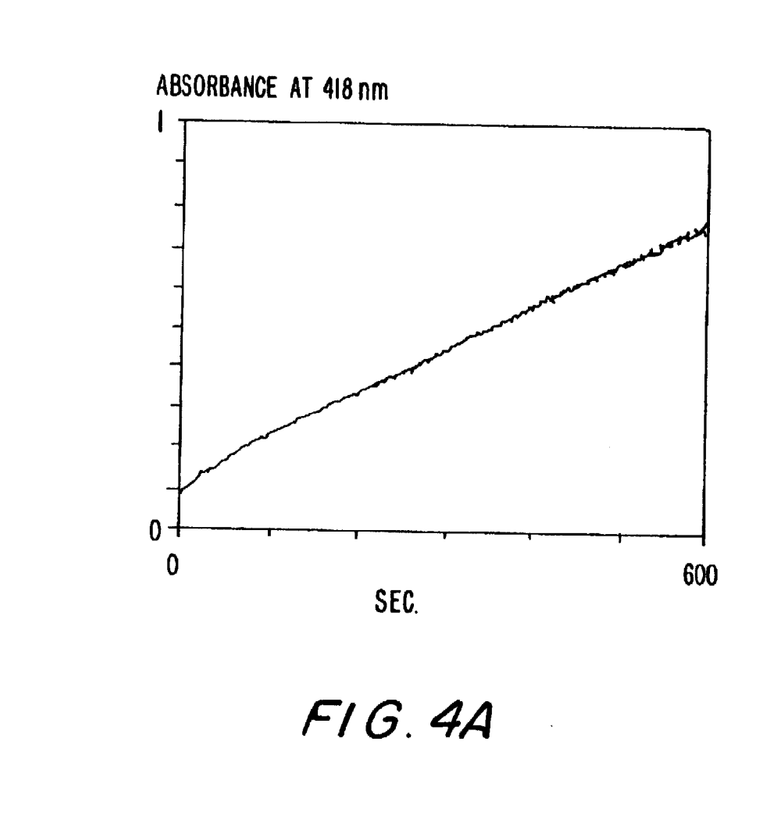
FIGS. 4A–4B show the effect of peroxidase combined with pHBS (accelerator) on the activity of an L-amino acid oxidase of the invention (4A in the absence of PHBS; 4B in the presence of 50 µM PHBS)
Figure 4B:
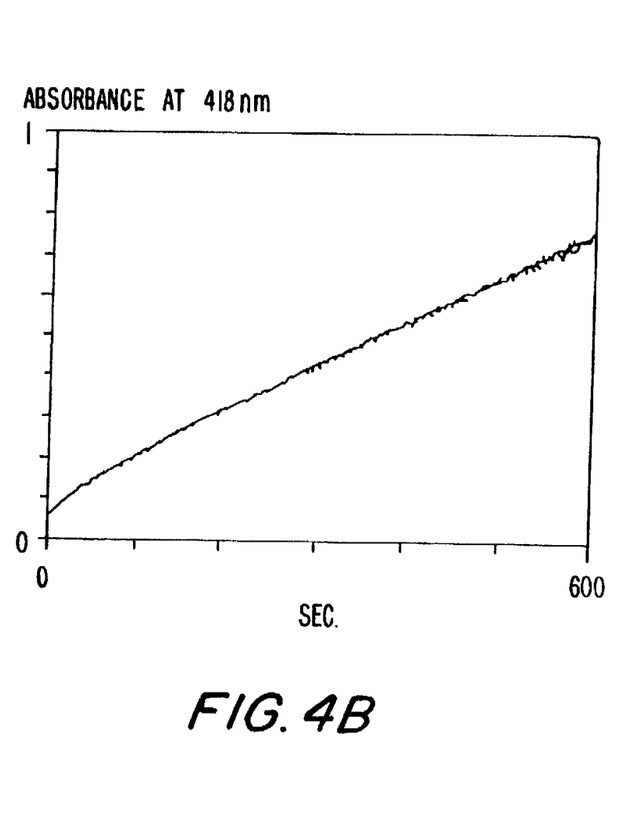

The results are presented in FIGS. 4A–4B, (4A in the absence of PHBS; 4B in the presence of 50 μM pHBS), where absorbance at 418 nm had been monitored at ambient temperature. As evidenced by these Figures, the activity of the L-amino acid oxidase of the invention is unaffected by the addition of pHBS.

EXAMPLE 5

Bleaching Example

This example demonstrates use of the L-amino acid oxidase obtained according to Ex. 1–2, in a process for bleaching of the dye Methyl Orange (obtained from Merck).

Bleaching of Methyl Orange was performed in a phosphate buffer at pH 8.5 and 35° C. The bleaching effect was monitored by the absorbance at 465 nm. For comparison the experiment was carried out with an initial addition of $H_2O_2$ as well as with L-amino acid oxidase and L-leucine. Both experiments were made in the presence as well as in the absence of pHBS as accelerator.

All experiments were performed with 10 nM of *Coprinus cinereus* peroxidase (CiP), obtained according to WO 92/16634.

Figure 5:
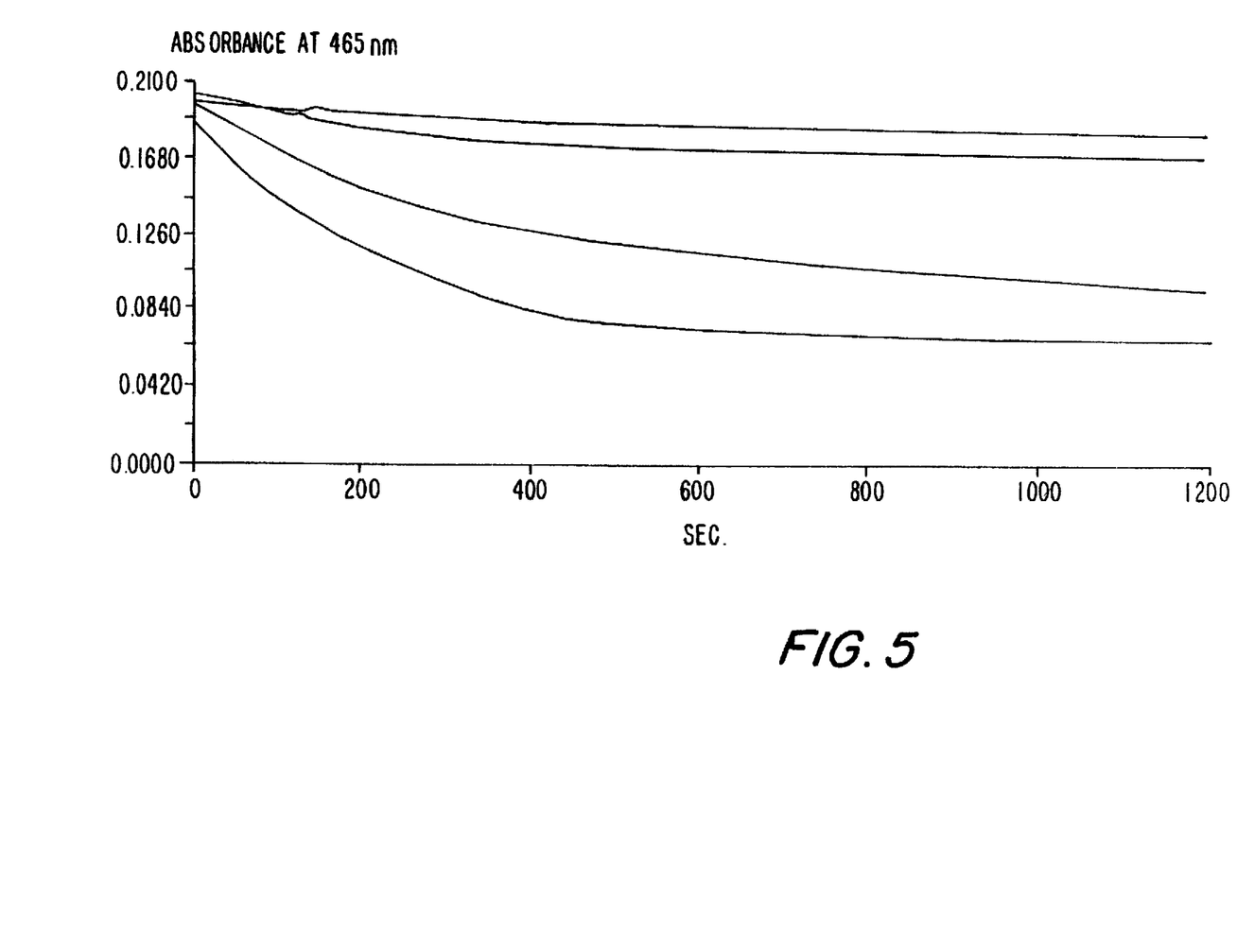
FIG. 5 shows bleaching of the dye Methyl Orange (8µM) with a *Coprinus cinereus* peroxidase (CiP) and hydrogen peroxide or L-amino acid oxidase (AAO) at pH 8.5 and 35° C. (timedrive in sec. at 465 nm; 1:10 nM CiP, 230 µM $H_2O_2$; 2:10 nM CiP, 1 mM L-leucine, 16 µg/ml AAO; 3:10 nM CiP, 53 µM pHBS, 1 mM L-leucine, 16 µg/ml AAO; 4:10 nM CiP, 53 µM PHBS, 230 µM $H_2O_2$)
Figure 6:
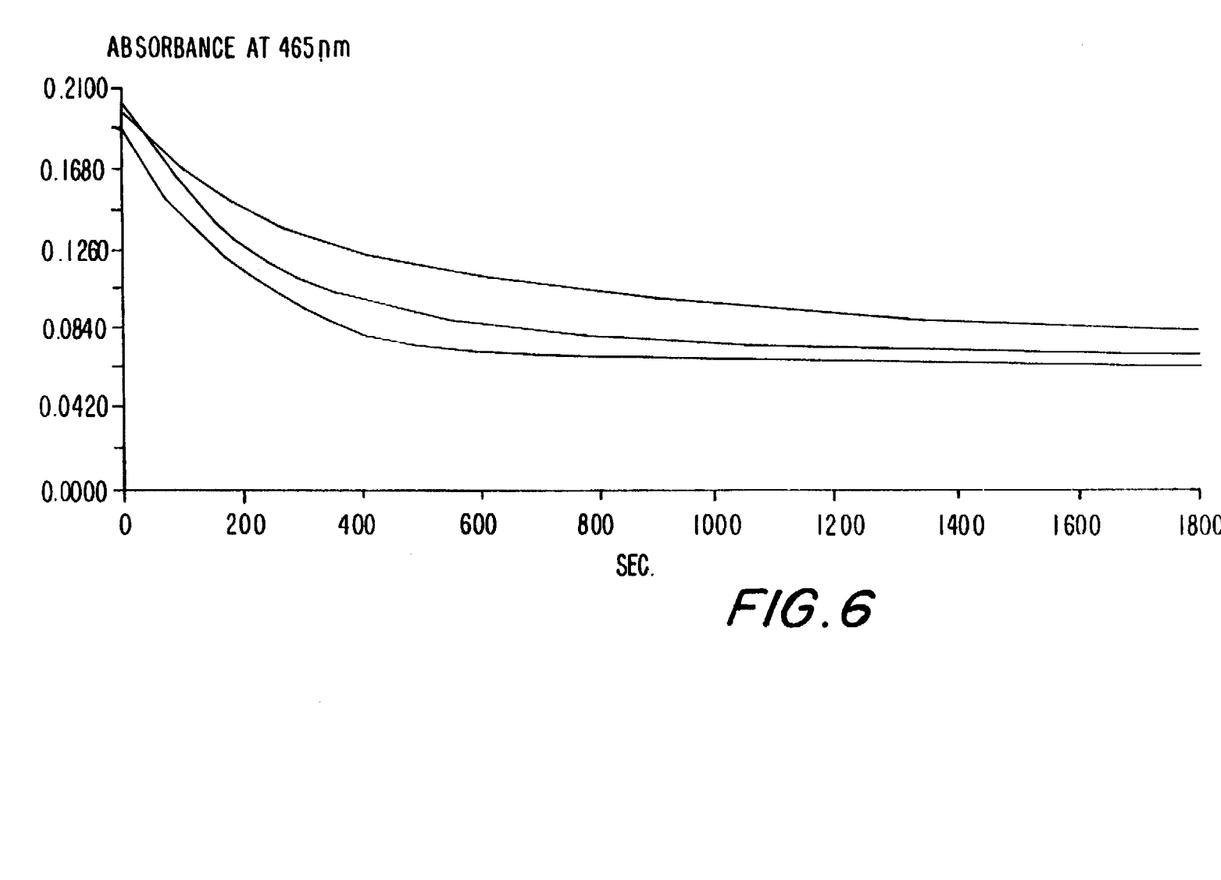
FIG. 6 shows bleaching of the dye Methyl Orange (8 µM) with a *Coprinus cinereus* peroxidase (CiP) and hydrogen peroxide or L-amino acid oxidase (AAO) at pH 8.5 and 35° C. (timedrive in sec. at 465 nm; 1:16 µg/ml AAO; 1 mM L-leucine; 2:32 µg/ml AAO, 1 mM L-leucine; 3:230 µM $H_2O_2$).

The results are presented in FIGS. 5–6. From these Figures it appears that by employing the L-amino acid oxidase of the invention (and its substrate) it is possible to achieve a bleaching effect similar to the effect obtained by addition of 230 μM of hydrogen peroxide.

We claim:

1. An L-amino acid oxidase E.C. 1.4.3.2 isolated from *Trichoderma harzianum* A611, CBS 223.93 and characterized by having the following properties:
   (A) pH optimum in the range of from pH 8.5 to 9.5 determined after incubation for 20 minutes at 20° C. in the presence of L-arginine;
   (B) pH stability of 80% or more, relative to initial activity, at pH 9.5 determined after incubation for 1 hour at 40° C. in the absence of substrate; and
   (C) activity towards L-arginine, L-lysine, L-methionine, L-asparagine, L-phenylalanine, and L-leucine.

2. A process for the preparation of an L-amino acid oxidase according to claim 1, which process comprises cultivation of an L-amino acid oxidase producing strain of *Trichoderma harzianum* AC11, CBS 223.93, in a suitable nutrient medium, containing carbon and nitrogen sources and inorganic salts, followed by recovery of the desired enzyme.

3. A process for in situ generation of hydrogen peroxide, comprising the step of adding the L-amino acid oxidase of claim 1 to a solution containing a substrate for said oxidase.

4. A detergent additive comprising an L-amino acid oxidase according to claim 1, wherein the detergent additive is in a form selected from the group consisting of a granulate, a non-dusting granulate, a liquid, a stabilized liquid, a slurry, or a protected enzyme.

5. A detergent additive according to claim 4, which further comprises a substrate for the oxidase.

6. A detergent composition comprising an L-amino acid oxidase according to claim 1, and comprising a substrate for the oxidase.

7. A detergent composition according to claim 6, which further comprises one or more other enzymes selected from the group consisting of proteases, lipases, amylases, cellulases, peroxidases, and other oxidases.

8. A detergent composition according to claim 7, in which the peroxidase is derived from *Coprinus*, or from *Bacillus*, or in which the peroxidase is derived from plants.

9. A process for inhibiting the transfer of a textile dye from a dyed fabric to another fabric when said fabrics are washed and/or rinsed together in a wash liquor, the process comprising adding an L-amino acid oxidase according to claim 1 to the wash liquor in which said fabrics are washed and/or rinsed.

10. A detergent composition according to claim 8, wherein the peroxidase is derived from one of *Coprinus cinereus*, *Coprinus macrorhizus*, *Bacillus pumilus*, or horseradish.

* * * * *

UNITED STATES PATENT AND TRADEMARK OFFICE
CERTIFICATE OF CORRECTION

PATENT NO. : 5,801,035
DATED : September 1, 1998
INVENTOR(S) : Schneider et al.

It is certified that error appears in the above-identified patent and that said Letters Patent is hereby corrected as shown below:

Abstract, line 3: delete "L phenylalanine" and insert --L-phenylalanine--.

Col. 2, lines 38, 39 and 46: delete "PHBS" and insert --pHBS--.

Col. 2, lines 60-63: "An L-amino acid oxidase preparation was subjected to characterization according to Example 3 of this specification." should be in paragraph form.

Col. 6, line 34: delete "11-18%"

Col. 6, line 35: after "(as $NaBO_3H_2O$)" insert --11.18%--.

Col. 9, line 47: delete "(as Na2SO$_4$)" and insert --(as $Na_2SO_4$)--.

UNITED STATES PATENT AND TRADEMARK OFFICE
CERTIFICATE OF CORRECTION

PATENT NO. : 5,801,035
DATED : September 1, 1998
INVENTOR(S) : Schneider et al.

It is certified that error appears in the above-identified patent and that said Letters Patent is hereby corrected as shown below:

Col. 12, lines 53 and 56: delete "PHBS" and insert --pHBS--.

Col. 13, line 17, claim 1: delete *"Trichodenna"* and insert --*Trichoderma*--.

Signed and Sealed this

Twenty-fifth Day of May, 1999

Attest:

Q. TODD DICKINSON

*Attesting Officer*  *Acting Commissioner of Patents and Trademarks*